United States Patent
Canney et al.

(10) Patent No.: US 11,135,455 B2
(45) Date of Patent: Oct. 5, 2021

(54) ULTRASONIC THERMAL ABLATION PROBE

(71) Applicant: CARTHERA, Paris (FR)

(72) Inventors: Michael Canney, Denver, CO (US);
Guillaume Bouchoux, Lyons (FR);
Alexandre Vignot, Lyons (FR);
Francois Lacoste, Paris (FR)

(73) Assignee: CARTHERA, Paris (FR)

( * ) Notice: Subject to any disclaimer, the term of this patent is extended or adjusted under 35 U.S.C. 154(b) by 410 days.

(21) Appl. No.: 16/093,718

(22) PCT Filed: Apr. 14, 2017

(86) PCT No.: PCT/EP2017/059047
§ 371 (c)(1),
(2) Date: Oct. 15, 2018

(87) PCT Pub. No.: WO2017/178641
PCT Pub. Date: Oct. 19, 2017

(65) Prior Publication Data
US 2019/0134429 A1    May 9, 2019

(30) Foreign Application Priority Data
Apr. 15, 2016  (FR) ...................................... 1653377

(51) Int. Cl.
*A61B 5/05*    (2021.01)
*A61N 7/02*    (2006.01)
(Continued)

(52) U.S. Cl.
CPC .............. *A61N 7/02* (2013.01); *B06B 1/0655* (2013.01); *A61B 17/2202* (2013.01);
(Continued)

(58) Field of Classification Search
None
See application file for complete search history.

(56) References Cited

U.S. PATENT DOCUMENTS 5,297,553 A    3/1994  Sliwa, Jr. et al.
5,620,479 A    4/1997  Diederich
(Continued)

FOREIGN PATENT DOCUMENTS

EP    2430996 A2    3/2012
EP    2731675 A1    5/2014
(Continued)

OTHER PUBLICATIONS

Canney, M. et al., "A multi-element interstitial ultrasound applicator for the thermal therapy of brain tumors", J. Acoust. Soc. Am., 134(2): 1647-1655, 2013.
(Continued)

*Primary Examiner* — Joel F Brutus
(74) *Attorney, Agent, or Firm* — BCF LLP

(57) ABSTRACT

The present invention relates to an ultrasonic probe for heating, internally, an ultrasonically absorbent target medium, the probe comprising: at least one piezoelectric transducer (21) having a front face (212) intended to be positioned facing the target medium and a back face (211) opposite the front face (212), the transducer being able to emit at least one primary wave emanating from its front face and at least one secondary wave emanating from its back face, the probe being noteworthy in that it furthermore comprises: a reflector (24) facing the back face (211) of the transducer (21), the reflector (24) being suitable for reflecting the secondary wave emitted by the transducer (21); and a cooling-fluid layer (25) between the transducer (21) and the reflector (24).

15 Claims, 5 Drawing Sheets

(51) Int. Cl.
*B06B 1/06* (2006.01)
*A61B 17/22* (2006.01)
*A61N 7/00* (2006.01)

(52) U.S. Cl.
CPC ............ *A61B 2017/22024* (2013.01); *A61N 2007/0047* (2013.01); *A61N 2007/0069* (2013.01); *A61N 2007/025* (2013.01)

(56) References Cited

U.S. PATENT DOCUMENTS

| | | | |
|---|---|---|---|
| 6,049,159 | A | 4/2000 | Barthe et al. |
| 6,106,474 | A | 8/2000 | Koger et al. |
| 6,537,306 | B1 | 3/2003 | Burdette et al. |
| 8,446,071 | B2 | 5/2013 | Kaminski et al. |
| 8,475,379 | B2 | 7/2013 | Thapliyal et al. |
| 8,851,080 | B2 | 10/2014 | Gowda et al. |
| 2006/0273695 | A1 | 12/2006 | Savage |
| 2007/0049828 | A1 | 3/2007 | Yao et al. |
| 2007/0167803 | A1* | 7/2007 | Kaminski ............ B06B 1/0677 600/459 |
| 2014/0257262 | A1 | 9/2014 | Carpentier et al. |
| 2015/0209551 | A1 | 7/2015 | Burdette et al. |
| 2016/0074017 | A1* | 3/2016 | Lee ............... A61B 8/5223 600/442 |

FOREIGN PATENT DOCUMENTS

| | | |
|---|---|---|
| WO | 2009125002 A1 | 10/2009 |
| WO | 2011053757 A1 | 5/2011 |
| WO | 2011146139 A1 | 11/2011 |
| WO | 2014121292 A1 | 8/2014 |
| WO | 2014145926 A1 | 9/2014 |

OTHER PUBLICATIONS

Kangasniemi, M. et al., "Multiplanar MR Temperature-Sensitive Imaging of Cerebral Thermal Treatment Using Intersitial Ultrasound Applicators in a Canine Model", J. Mag. Res. Imag., 16(5): 522-531, 2002.

Leedom, D. A. et al., "Equivalent Circuits for Transducers Having Arbitrary Even- or Odd-Symmetry Piezoelectric Excitation", IEEE Transactions on Sonics and Ultrasonics, vol. 18, No. 3, pp. 128-141, 1971.

Sherrit, S. et al., "Comparison of the Mason and KLM Equivalent Circuits for Piezoelectric Resonators in the Thickness Mode", IEEE Ultrasonics Symposium, pp. 921-926, 1999.

Lethiecq, M. et al., "Measurement of losses in five piezoelectric ceramics between 2 and 50 MHz"IEEE Transactions on Ultrasonics, Ferroelectrics and Frequency Control, vol. 40, No. 3, pp. 232-237, 1993.

PCT International Search Report and Written Opinion of International Searching Authority for International Patent Application No. PCT/EP2017/059047 (14 pages).

* cited by examiner

ULTRASONIC THERMAL ABLATION PROBE

CROSS-REFERENCE TO RELATED APPLICATIONS

This application is a national phase filing under 35 U.S.C. § 371 of International Application No. PCT/EP2017/059047 filed on Apr. 14, 2017, which claims benefit of priority from French Patent Application No. 1653377 filed Apr. 15, 2016, the contents of which are hereby incorporated by reference in their entirety.

FIELD OF THE INVENTION

The present invention relates to the general technical field of ultrasonic tissue treatment, and in particular the technical field of ultrasonic emission devices.

More precisely, the present invention relates to interstitial probes for the treatment by hyperthermia of a target zone—such as a malignant tumor—localized using high-intensity ultrasonic waves.

BACKGROUND OF THE INVENTION

1. General

Therapeutic ultrasound is used today in numerous applications, in particular to allow the ablation of undesirable tissue or tumors.

An external ultrasonic treatment device has already been proposed. Such a device conventionally includes one (or more) transducer(s) for generating high-intensity focused ultrasound toward a target zone. The ultrasonic transducer(s) is(are) designed to concentrate acoustic energy in depth in the body of the patient in order to induce heating and destruction of a target tissue in a non-invasive approach.

Also proposed is an internal ultrasonic treatment device designed to be put into contact with the target zone to be treated. Such an internal treatment device—known by the name of "intra-tissue ultrasonic applicator"—allows the treatment of zones that are inaccessible externally. This device includes one (or more) transducer(s) mounted on a small-diameter cylindrical support (i.e. 2 to 3 mm) to allow their application interstitially, or through a catheter. Each transducer can have a flat, spherical or cylindrical surface, and a general rectangular shape. It allows the application of acoustic powers comprised between 1 and 50 W/cm$^2$ (preferably between 10 and 30 W/cm$^2$) by generating divergent or slightly convergent ultrasonic waves through target tissues.

The effectiveness of treatment by hyperthermia depends on the application time of the ultrasonic waves by means of the intra-tissue applicator. A tissue is permanently damaged in less than a second if its temperature reaches more than 55° C. Any temperature higher than 41° C. can damage living tissue, depending on the duration of the hyperthermia. The concept of a "thermal dose" is used to quantify the risk of tissue damage, and a thermal dose of more than 240 minutes at 43° C. is generally considered lethal.

In order to limit the number of re-positionings of the applicator necessary for the treatment of a large volume, it is generally desirable to be able to heat tissue as far as possible (typically 10 to 30 mm) from the applicator.

To accomplish this, it is necessary to increase the acoustic power produced by the transducer while limiting the risks of degradation thereof.

2. Existing Solutions for Increasing the Effectiveness of the Treatment

To increase the acoustic power produced by the transducer of the intra-tissue applicator, different solutions have already been proposed.

2.1. A Layer of Air on the Rear Face of the Transducer

For example, an applicator has already been proposed including a layer of air between the transducer and the cylindrical support of the transducer. This layer of air allows a reduction in the quantity of energy lost during the activation of the transducer by reflecting all the acoustic energy generated by the transducer in the direction of the support.

In fact, a transducer is a piezoelectric element comprising:
a front face extending facing the target zone to be treated, and
a rear face extending facing the support of the applicator.

During the activation of the transducer, it converts the electrical energy into mechanical energy and its vibration generates an acoustic wave which can propagate toward the front and toward the rear of the transducer.

A layer of air on the rear face of the piezoelectric element acts as a mirror and reflects the wave directed toward the rear of the transducer in the direction of the front face of the transducer. Thus, the loss of a portion of the mechanical energy generated by the transducer in the rear medium is prevented.

One disadvantage, however, of this type of applicator relates to the heating of the transducer. In fact, the electro-acoustic efficiency of piezoelectric elements is generally on the order of 60 to 70%. Thus 30 to 40% of the electrical energy provided to a piezoelectric transducer is dissipated in the form of heat through the transducer. This induces a considerable increase in the temperature within the transducer.

This heating of the transducer can induce its deterioration. Moreover, the heating of the transducer can reduce the depth of penetration of the ultrasound, due to the boiling of the propagation medium in proximity to the surface of the transducer. In fact, the presence of gas bubbles prevents the propagation of ultrasonic energy and can cause the undesirable destruction of collateral healthy tissues by thermal diffusion.

2.2. Cooling System on the Rear Face of the Transducer
To limit the risks:
of deterioration of the transducer and
of vaporization of tissues in proximity and/or in contact with the transducer, an intra-tissue applicator has already been proposed which includes a cooling system on the front face of the transducer.

Also known are applicators including a cooling system on the rear face of the transducer to allow better control of tissue heating by limiting the risks of undesirable heating by thermal conduction from the transducer to the tissue.

One disadvantage, however, of the solution described above is that the presence of the cooling system tends to reduce the effectiveness of in-depth treatment in a given direction. In fact, a portion of the acoustic energy generated by the piezoelectric element is directed toward the rear of the transducer.

3. Aim of the Invention

One aim of the invention is to propose an interstitial probe for the treatment of a target zone by hyperthermia allowing at least one of the aforementioned disadvantages to be mitigated.

More precisely, aim of the present invention is to propose an interstitial probe allowing the generation of high acoustic powers with respect to the bulk of the probe, and to avoid overheating and vaporizing tissues in contact with the probe, allowing faster, more effective and safer treatments. To this end, an interstitial probe is proposed:
- having an electro-acoustic conversion efficiency comparable to that of an intra-tissue applicator including a layer of air on the rear face of the transducer,
- including an effective cooling system with a small bulk.

BRIEF DESCRIPTION OF THE INVENTION

To this end, the invention proposes an ultrasonic probe for heating, internally, an ultrasonically absorbent target medium, the probe comprising:
- at least one piezoelectric transducer including a front face designed to be positioned facing the target medium and a rear face opposite to the front face, the transducer being capable of emitting at least one primary wave emanating from its front face and at least one secondary wave emanating from its rear face,
- a reflector extending facing the rear face of the transducer, the reflector being designed to reflect the secondary wave emitted by the transducer,
- a layer of cooling fluid between the transducer and the reflector, noteworthy in that the thickness of the layer of cooling fluid is designed based on:
  - the material constituting the cooling fluid,
  - the thickness and the material constituting the reflector,
  - the nominal frequency of the transducer, so that a secondary ultrasonic wave reflected by the reflector and propagating toward the front face interferes constructively with a primary ultrasonic wave emanating from the front face of the transducer.

Thus, the invention offers the possibility of having a cooling by using a cooling fluid—such as water—on the rear face(s) of the transducer(s) while retaining an electro-acoustic conversion efficiency as high as that of intra-tissue applicators of which the rear face is cooled by air.

This makes it possible to obtain an interstitial probe for treatment by hyperthermia with increased effectiveness, which allows its miniaturization. This new arrangement allows the effectiveness of the probe to be maximized in terms:
- of electroacoustic conversion on the one hand, and
- of cooling the transducers, on the other hand.

The optimizations applied to the probe according to the invention allow the acceleration of the duration of the treatments performed. In fact, the fact of cooling the transducers with a cooling fluid allows an increase in the duration of activation of the transducers (in particular, it is not necessary to deactivate the transducers for a certain period to allow their cooling). Moreover, effective cooling of the transducers allows an increase in the maximum acoustic power that the probe can emit, which is mainly limited by the overheating of the piezoelectric element bringing about its deterioration. Increased acoustic power emitted by the probe allows a reduction in the treatment time and the treatment of a larger volume.

Preferred but non-limiting aspects of the treatment probe according to the invention are the following:
The transducer can be supplied with electrical power by an electrical excitation signal inducing the emission by said transducer of ultrasonic waves at a nominal frequency comprised between 3 and 10 MHz, the reflector being designed to reflect at least 80% of the acoustic energy of the secondary wave emitted by the transducer at the nominal frequency of the transducer, and the cooling fluid having an acoustic attenuation coefficient of less than 1 dB/cm at the nominal frequency of the transducer, preferably less than 0.1 dB/cm at the nominal frequency of the transducer;

Depending on the thickness and on the material constituting the reflector, the thickness of the layer of cooling fluid can be:
- either equal to an odd multiple of one-quarter of the wavelength of the secondary ultrasonic wave in the constitutive material of the cooling liquid,
- or equal to an integer multiple of one-half of the wavelength of the secondary ultrasonic wave in the constitutive material of the cooling fluid.

In a variant embodiment of the probe:
- the acoustic impedance of the material constituting the reflector is greater than $10^7$ kg/(m²s), and
- the thickness of the layer of cooling fluid is equal to an odd multiple of one-quarter of the wavelength of the secondary ultrasonic wave in the constitutive material of the cooling fluid.

The thickness of the reflector can be greater than or equal to 20 μm, preferably greater than 30 μm, and even more preferably greater than 40 μm.

The reflector can comprise an internal wall including a first face facing the rear face of the transducer and a second, opposite face, the second face being in contact with air;

In one variant embodiment of the probe:
- the acoustic impedance of the material constituting the internal wall is comprised between $1 \times 10^6$ kg/(m²s) and $10 \times 10^6$ kg/(m²s),
- the thickness of the internal wall is equal to an odd multiple of one-quarter of the wavelength of the secondary ultrasonic wave in the material constituting the internal wall, and
- the thickness of the layer of cooling fluid is equal to an odd multiple of one-quarter of the wavelength of the secondary ultrasonic wave in the cooling fluid;

In one variant embodiment of the probe:
- the acoustic impedance of the material constituting the internal wall is comprised between $1 \times 10^6$ kg/(m²s) and $10 \times 10^6$ kg/(m²s), and
- the thickness of the internal wall and the thickness of the layer of cooling fluid are not comprised in ranges of more or less 25% around an integer multiple of one-half of the wavelength of the secondary ultrasonic wave in the material constituting the internal wall;

In one variant embodiment of the probe:
- the acoustic impedance of the material constituting the internal wall is comprised between $1 \times 10^6$ kg/(m²s) and $10 \times 10^6$ kg/(m²s),
- the thickness of the internal wall is equal to an integer multiple of one-half of the wavelength of the secondary ultrasonic wave in the material constituting the internal wall,
- the thickness of the layer of cooling fluid is equal to an integer multiple of one-half of the wavelength of the secondary ultrasonic wave in the cooling fluid;

In one variant embodiment of the probe:
- the acoustic impedance of the material constituting the internal wall is comprised between $1 \times 10^6$ kg/(m²s) and $10 \times 10^6$ kg/(m²s), and
- the thickness of the internal wall and the thickness of the cooling fluid are not comprised in ranges of more or less 25% around an odd multiple of one-quarter of the wavelength of the secondary ultrasonic wave in the material constituting the internal wall.

The probe can also comprise an adaptation layer—composed of parylene for example—on the front face of the transducer, said adaptation layer having a thickness equal to a multiple of one-quarter of the wavelength of the ultrasonic wave in the constitutive material of said adaptation layer—for example substantially equal to 80 µm for a central resonance frequency equal to 6 MHz.

The optimization of the thickness of the layer of cooling fluid allows, on the one hand, limiting the bulk of the probe, and on the other hand improving the efficiency of the transducers, and therefore increasing the acoustic power that they can emit to accelerate treatment and increase the depth of penetration.

BRIEF DESCRIPTION OF THE DRAWINGS

Other advantages and features of the probe according to the invention will be revealed more clearly by the description that follows of several variant embodiments, given by way of non-limiting example, based on the appended drawings in which.

DETAILED DESCRIPTION OF THE INVENTION

1. General

Figure 1:
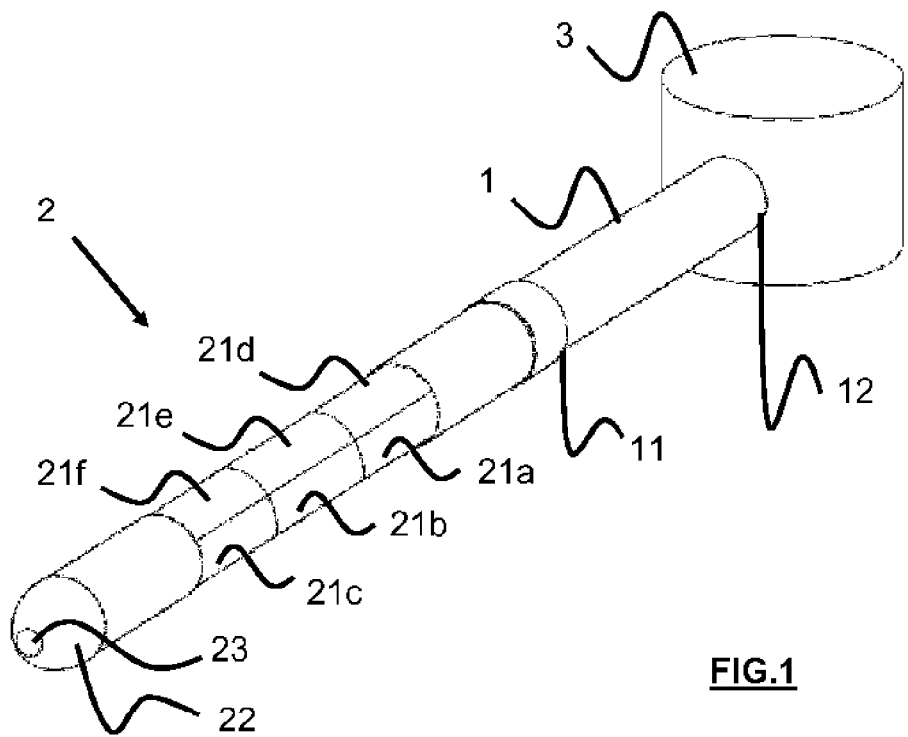
FIG. 1 illustrates schematically an example of a probe for hyperthermia treatment of a target zone.

With reference to FIG. 1, one example of probe for the hyperthermia treatment of a target zone is illustrated. The probe—or applicator—is designed to be introduced into the body of a patient to allow the treatment of the target zone. The diameter of the probe is preferably less than 5 mm (in particular equal to 3.5 mm) to facilitate its introduction into the interior of the patient interstitially or through a catheter.

The probe comprises:
a flexible longitudinal body 1 with a generally cylindrical shape,
an active portion 2 mounted at a distal end 11 of the body 1, the active portion 2 including one (or more) ultrasonic transducer(s) 21a-21f,
a junction box 3 mounted at a proximal end 12 of the body 1 to electrically connect the active portion to a remote control unit allowing control of the transducer(s) 21a-21f.

1.1. Body

The body 1 can be composed of a flexible sleeve made in a material selected for its non-toxic and high tolerance characteristics.

The body 1 can comprise one or more channels, possibly coaxial, for the passage:
of one (or more) electrical cables for electrically connecting the transducer(s) to the control unit 5,
of a cooling fluid, and/or
of a surgical tool allowing the performance of a biopsy, etc.

The structure of the body 1 being known per se by a person skilled in the art, it will not be described in more detail hereafter.

1.2. Control Unit 5

Figure 2:
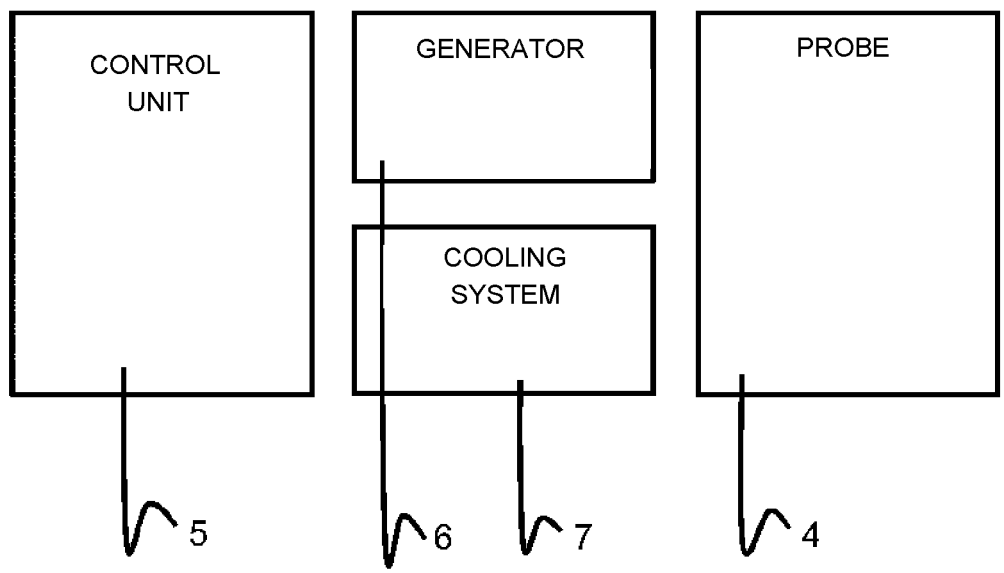
FIG. 2 illustrates a complete system including the treatment probe.

With reference to FIG. 2, the control unit 5 allows the control of the ultrasonic transducer(s) 21a-21f, and possibly processing the signals received from detectors mounted on the active portion 2 of the probe 4.

The control unit 5 is connected to a generator 6 to supply electrical power to the transducers 21a-21f and to data entry means for specifying the parameters—such as frequency and/or power, etc.—of the electrical current supplying the transducer(s) 21a-21f.

The control unit 5 is also connected to a cooling system 7 for supplying cooling fluid to the active portion 2 of the probe 4.

The constitutive elements of the control unit 5 can be produced in a programmed or cabled manner. The different circuits constituting the control unit 5 are known per se and will not be described more accurately.

1.3. Active Portion 2

The active portion 2 has a generally cylindrical shape.

It comprises a spherically shaped or conical head 22 for facilitating the insertion of the probe into the body of the patient. The head 22 can have a through opening 23 for the passage of a biopsy tool.

The active portion 2 also comprises:
one (or more) ultrasonic transducer(s) 21a-21f mounted on its lateral wall,
one (or more) acoustic reflector(s) mounted facing one (or more) rear face(s) of the transducer(s) 21a-21f, and
a cooling fluid flowing between the reflector(s) and the transducer(s).

The combined presence:
of a reflector on the rear face of each transducer, and
of a cooling fluid between the reflector(s) and the transducer(s) allows an increase in the treatment effectiveness of the probe while still ensuring its cooling.

In fact, each transducer 21a-21f comprises a front face designed to face the target zone to be treated and a rear face opposite to the front face. Upon activation of the transducer, it converts the electrical energy supplied to it:
into primary acoustic waves propagating toward the exterior of the active portion (i.e. propagation toward the front of the transducer), and
into secondary waves propagating toward the interior of the active portion (i.e. propagation toward the rear of the transducer).

The presence of the acoustic reflector disposed facing the rear face of each transductor allows the secondary ultrasonic waves to be reflected toward the exterior of the active portion (i.e. in the direction of the target zone). Thus these reflected secondary ultrasonic waves combine with the primary ultrasonic waves, which allows an increase in the quantity of acoustic energy useful in the treatment of the target zone.

In addition, the presence of a cooling fluid allows the local heating of each transducer to be limited, which reduces the risks of gas bubble formation which might prevent the propagation of ultrasonic energy generated by each transducer.

The features of the different elements constituting the active portion 2 will now be described in more detail.

1.3.1. Transducer 21

Each transducer 21a-21f can be flat, convergent (concave), or divergent (convex).

Transducers that are flat, slightly focused or divergent have the advantage of being particularly suited to interstitial application for bringing the transducer as close as possible to the target tissue to be treated.

Each transducer 21a-21f can be composed of a piezoelectric element with a rectangular (flat transducer), cylindrical or cylindrical portion (divergent transducer) shape. The nominal resonance frequency of each transducer 21a-21f is comprised between 250 kHz and 21 MHz, preferably comprised between 3 and 10 MHz (and even more preferably between 4 and 6 MHz). The acoustic power emitted by these types of transducers is a few tens of watts per square centimeter ($W/cm^2$).

Hereafter in the description, the invention will be described more precisely with reference to the use of one (or more) divergent transducer(s), it being well understood that the invention could be applied to the use of one (or more) flat transducer(s).

The active portion 2 can comprise a single tubular one-piece transducer. The use of a tubular transducer makes it possible to facilitate the manufacture of the treatment probe, this type of transducer being robust and easy to glue and to weld. The transducer comprises:
- an interior electrode forming the rear face (i.e. the internal face of the tube) and
- an exterior electrode forming the front face of the tubular transducer (i.e. the external face of the tube).

As a variant, the active portion can comprise a plurality of distinct transducers, each transducer having the shape of a portion of a cylinder, the transducers being disposed with respect to one another to form a tubular assembly. This assembly of transducers can be obtained by segmentation of a tubular one-piece transducer. The segmentation method can consist of sectioning the exterior electrode of the tubular one-piece transducer based on its height and/or its circumference.

For example, in the embodiment illustrated in FIG. 1, the active portion 2 comprises three annular patterns of transducers disposed along the longitudinal axis of the active portion 2, each annular pattern being composed of four transducers shaped like quarter cylinders disposed radially around the lateral wall of the active portion 2.

1.3.2. Reflector 24

The acoustic reflector allows the reflection of the secondary ultrasonic waves propagating from the rear face of each transducer.

The reflector is preferably tubular and comprises:
- an exterior convex face facing the rear face of the transducer, and
- an interior concave face opposite to the exterior face.

The reflector allows the reflection, in the direction of the front face of the transducer, of the ultrasonic waves propagating toward the rear. The material constituting the reflector depends on the general structure of the probe.

For example, in certain embodiments, the reflector is a material of low acoustic impedance, such as an assembly composed of a gas and of a layer of polyether ether ketone (hereafter designated "PEEK").

In other embodiments, the reflector comprises a layer of material with a high acoustic impedance, such as metal (brass, etc.) or ceramic.

The reflector is preferably selected so as to reflect at least 90% of the incident acoustic energy at the nominal frequency of each transducer, and preferably at least 95% of the incident acoustic energy at the nominal frequency of each transducer.

1.3.3. Cooling Fluid 25

The cooling fluid allows limiting the heating of each transducer. The cooling fluid can be a liquid (such as water), a heat-transfer gel, etc.

Advantageously, the cooling fluid has an acoustic attenuation of less than one decibel per centimeter (1 dB/cm) at the nominal frequency of each transducer, and preferably less than one-tenth of a decibel per centimeter (0.1 dB/cm). This allows maximizing the quantity of acoustic energy re-directed by the reflector toward the exterior of the probe.

1.3.4. Dimensioning

Advantageously, the thicknesses:
- of the reflector on the one hand, and
- of the layer of cooling fluid, on the other hand can be selected to maximize the equivalent coefficient of reflection at the rear face of the piezoelectric element at the operating frequency. For this purpose, the thicknesses can be selected so that the secondary ultrasonic waves reflected by the reflector and propagating toward the front face interfere constructively with the primary ultrasonic waves emanating from the front face of the transducer and propagating toward the exterior of the probe.

More precisely, the dimensions of the layer of fluid and of the acoustic reflector are selected so that the primary and secondary waves are in phase at the front face of each transducer so as to create an amplification effect of the acoustic waves propagating toward the exterior of the probe at the operating frequency.

This makes it possible to maximize the acoustic energy emitted toward the target zone, and therefore maximizes the effectiveness of the treatment probe.

As will appear more clearly from the description that follows, the thicknesses of the reflector and of the fluid layer are selected depending on:
- the material constituting the cooling fluid,
- the material constituting the internal wall,
- the nominal frequency of each transducer.

2. Principle

Figure 3:
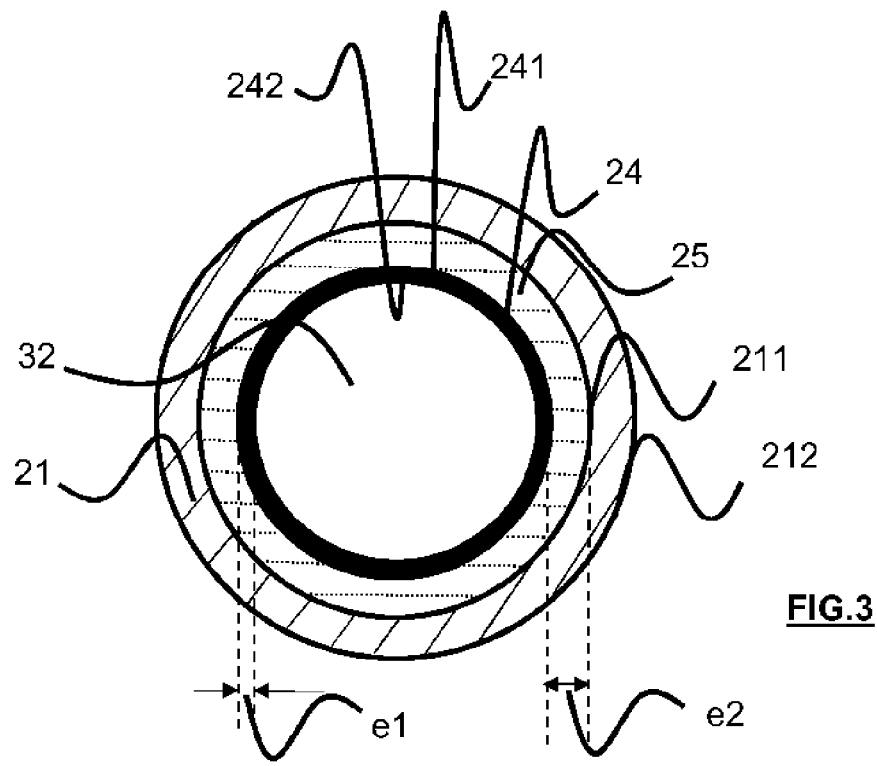
FIGS. 3 to 5 are cross section views of different embodiments of an active portion of a treatment probe.

With reference to FIG. 3, the basic structure of the active portion 2 is illustrated.

The active portion 2 comprises a single one-piece tubular transducer 21, a tubular internal wall 24, a cooling fluid 25 between the transducer 21 and the internal wall 24.

The transducer 21 comprises an interior electrode forming a rear face 211 (i.e. the internal face of the tube) connected to ground and an exterior electrode forming a front face 212 (i.e. the external face of the tube). The transducer 21 has a diameter of 3.5 mm and a height of 10 to 40 mm.

The internal tubular wall 24 extends in the interior of the tubular transducer 21. The internal wall 24 comprises a first face 241 facing the rear face 211 of the transducer 21 and a second, opposite face 242. Advantageously, the internal wall 24 is positioned on the active portion 2 so that the axes of revolution of the transducer 21 and of the internal wall 24 are coaxial. The internal wall 24 ca be made of various materials. For example, a material with a high impedance such as alumina or a metal such as copper or steel.

It can also be made of a material with a relatively low impedance—such as PEEK—with an acoustic impedance comprised between $1 \times 10^6$ kg/($m^2$s) and $10 \times 10^6$ kg/($m^2$s). In this case, the material 32 situated in the interior of the wall 24 must include a very low impedance, for example air or a gas, so that the wall 24—material 32 assembly behaves as a rear wave reflector.

The internal wall 24 has a thickness e1.

The cooling fluid 25 is a heat-transfer fluid situated at or flowing between the rear face of the transducer 21 and the first face of the internal wall 24. In the embodiment illustrated in FIG. 3, the cooling fluid 25 consists of a layer of water with thickness e2.

The presence of the cooling fluid in the interior of the active portion 2 allows the discharge or the storage of the heat generated at the transducer 21.

Advantageously, the thicknesses e1, e2 of the internal wall 24 and of the cooling fluid layer 25 can be optimized so that the acoustic energy reflected by the reflector arrives in phase on the surface of the transducer 21.

2.1. Case of a Low-Acoustic-Impedance Reflector (PEEK-air Assembly):

2.1.1. Configuration 1

When the reflector has a low acoustic impedance (for example a reflector composed of a gas and of a layer of PEEK), the thickness e1 and of the internal wall 24 can be selected equal to an odd multiple of one-quarter of the wavelength in the material of the internal wall—in order to maximize the reflection of the pressure wave in the cooling fluid 25 on the external wall of 24, at the operating frequency.

In order for the acoustic wave reflected by the reflector to arrive in phase with the wave propagating forward to the surface of the transducer 21, the thickness e2 of the layer 25 of the cooling fluid (corresponding to the distance between the internal wall and the transducer) can be selected equal to an odd multiple of one-quarter of the wavelength of the secondary ultrasonic wave in the cooling fluid.

Typically, if the cooling fluid is water, the nominal frequency of the transducer is 6 MHz, and the reflector is composed of a gas and a layer of PEEK, then the thickness e2 of the layer of cooling fluid 25 can be equal to 63 μm, 189 μm, 315 μm, etc., and the thickness of the internal tube made of PEEK can be 108 μm, 324 μm, 540 μm . . . .

2.1.2. Configuration 1bis

As a variant, the thicknesses e1 and e2 can be selected equal to a multiple of one-half of the wavelength in the corresponding material.

Typically, if the cooling fluid is water and the nominal frequency of the transducer 21 is 6 MHz, then the thickness e2 of the layer of cooling fluid 25 can be equal to 125 μm, 250 μm, 375 μm, etc.

The optimization of the thickness of the layer 25 of cooling fluid leads to increased effectiveness of the treatment probe which can approach the effectiveness of a probe having a layer of air on the rear face 211 of the transducer 21.

2.2. Case of a Reflector with High Acoustic Impedance (Configuration 2)

When the reflector comprises a layer of material with high acoustic impedance—i.e. an acoustic impedance higher than $10^{-7}$ kg/(m²s) such as alumina or brass or stainless steel—the thickness e1 can be selected equal to an odd multiple of one-quarter of the wavelength in the material of the internal wall—so as to maximize the reflection of the pressure wave in the cooling fluid 25 on the external wall of 24, at the operating frequency.

This thickness depends on the material of the internal wall 24. For example, if the material of the internal wall 24 is copper, the thickness must be at least 20 microns (FIG. 6A).

Figure 6A:
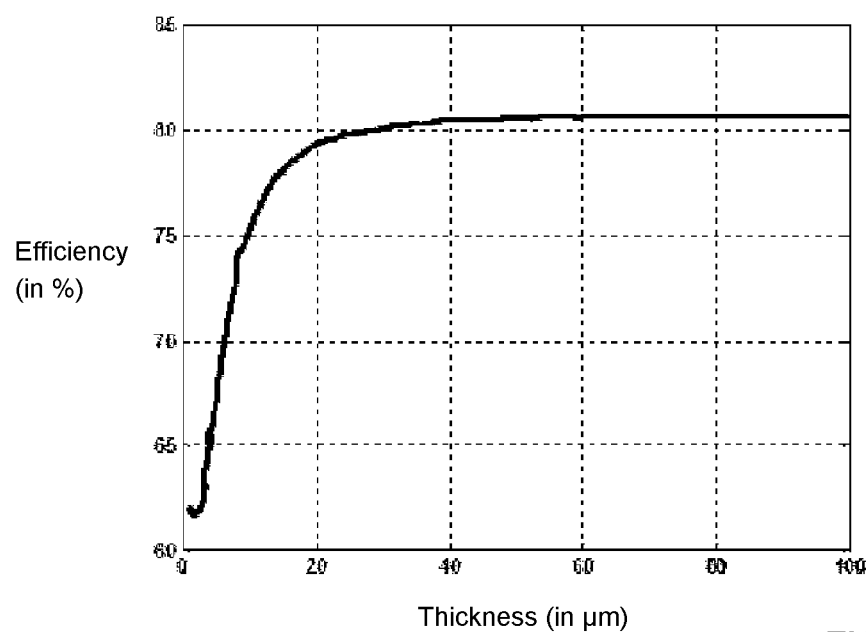
FIGS. 6A to 6C are curves illustrating the effectiveness of a treatment probe.

In fact, as shown in FIG. 6A which illustrates the effectiveness of the transducer depending on the thickness e1 of the reflector for a nominal frequency of the transducer equal to 6 MHz, the effectiveness of the transducer is a maximum when the thickness of the reflector is greater than 20 μm. This is explained by the fact that, when the thickness of the reflector is greater than 20 μm, it reflects the totality of the secondary acoustic waves emanating from the rear face of the transducer.

In order for the acoustic energy reflected by the reflector to arrive in phase at the surface of the transducer, the thickness e2 of the layer of cooling fluid (corresponding to the distance between the internal wall and the transducer) is selected equal to an odd multiple of one-quarter of the wavelength of the secondary ultrasonic wave in the cooling fluid.

Typically, if the cooling fluid is water and the nominal frequency of the transducer is 6 MHz, then the thickness of the layer of cooling fluid can be equal to 63 μm, 189 μm, 315 μm, etc.

The optimization of the thickness e2 of the layer 25 of cooling fluid leads to increased effectiveness of the treatment probe at the operating frequency.

2.3. Optimization of the Thicknesses of the Reflector and of the Layer of Cooling Fluid In each of the configurations described previously, the transducer is cooled by using a cooling fluid the thickness e2 of which is optimized so that the wave reflected by the reflector arrives in phase on the transducer. This allows optimizing the effectiveness of the acoustic emission.

The same is true of the thickness e1 of the reflector which is selected so that the secondary acoustic waves reflected by the reflector arrive in phase at the surface of the transducer, which leads to increased effectiveness of the treatment probe.

The table below illustrated examples of the thicknesses e1, e2 optimized for the different configurations 1, 2 and 1bis of the treatment probe, at 6 MHz.

| configuration | Thickness e2 of the layer of cooling fluid, in the case of water | Thickness e1 of the internal tube | Material constituting the internal tube | Material facing the 2nd face of the internal tube | Maximum effectiveness at a nominal frequency of 6 MHz |
|---|---|---|---|---|---|
| 1 | $(2N+1)\dfrac{\lambda_{eau}}{4}$ <br> 189 μm | $(2N+1)\dfrac{\lambda}{4}$ <br> 108 μm | PEEK <br> λ = 431 μm <br> Z = 3.23 MR | Air | 81% |

-continued

| configuration | Thickness e2 of the layer of cooling fluid, in the case of water | Thickness e1 of the internal tube | Material constituting the internal tube | Material facing the 2nd face of the internal tube | Maximum effectiveness at a nominal frequency of 6 MHz |
|---|---|---|---|---|---|
| 2 | $(2N+1)\dfrac{\lambda_{eau}}{4}$<br>189 µm | $(2N+1)\dfrac{\lambda}{4}$<br>417 µm (N = 0) | Alumina<br>$\lambda$ = 1667 µm<br>Z = 39.8 MR | Water or air | 81% |
| 1 bis | $N\dfrac{\lambda_{eau}}{2}$<br>125 µm | $N\dfrac{\lambda}{2}$<br>216 µm | PEEK<br>$\lambda$ = 431 µm<br>Z = 3.23 MR | Air | 79% |

In practice, it is possible to deviate from the thicknesses recommended in this table, and retain good efficiency; it is especially important to note the "prohibited" thicknesses for which the effectiveness of the tube is low (FIG. 6)

The thicknesses recommended in this table are only indicative and can be optimized experimentally (it is only a simple model that is used for this table, and the parameters of the materials used for this model are only indicative)

Figure 6B:
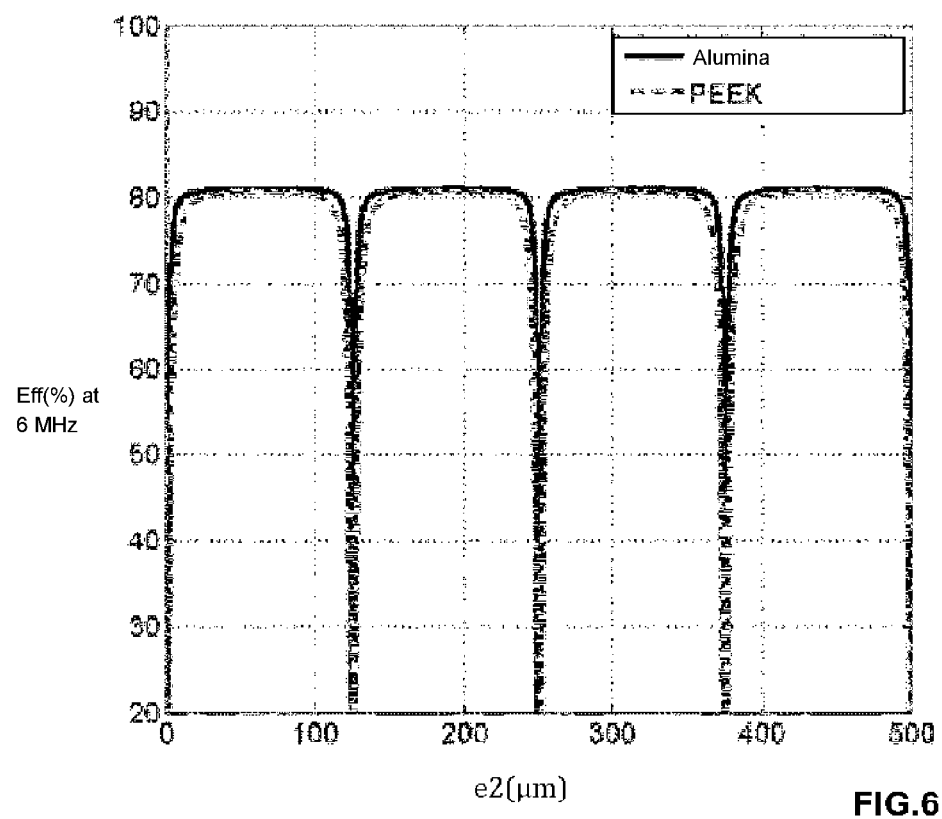

FIG. 6B illustrates the calculated reflectivity as a function of e1 for configurations 1 and 2. It covers a larger range of thicknesses, which highlights the drop in reflectivity near 840 microns (config 2, alumina). Note that it is obtained with an optimal thickness e2 of the layer of cooling fluid of 189 µm (3*lambda/4 as in the table, but otherwise 63 µm, i.e. lambda/4, would give the same curves)

Figure 6C:
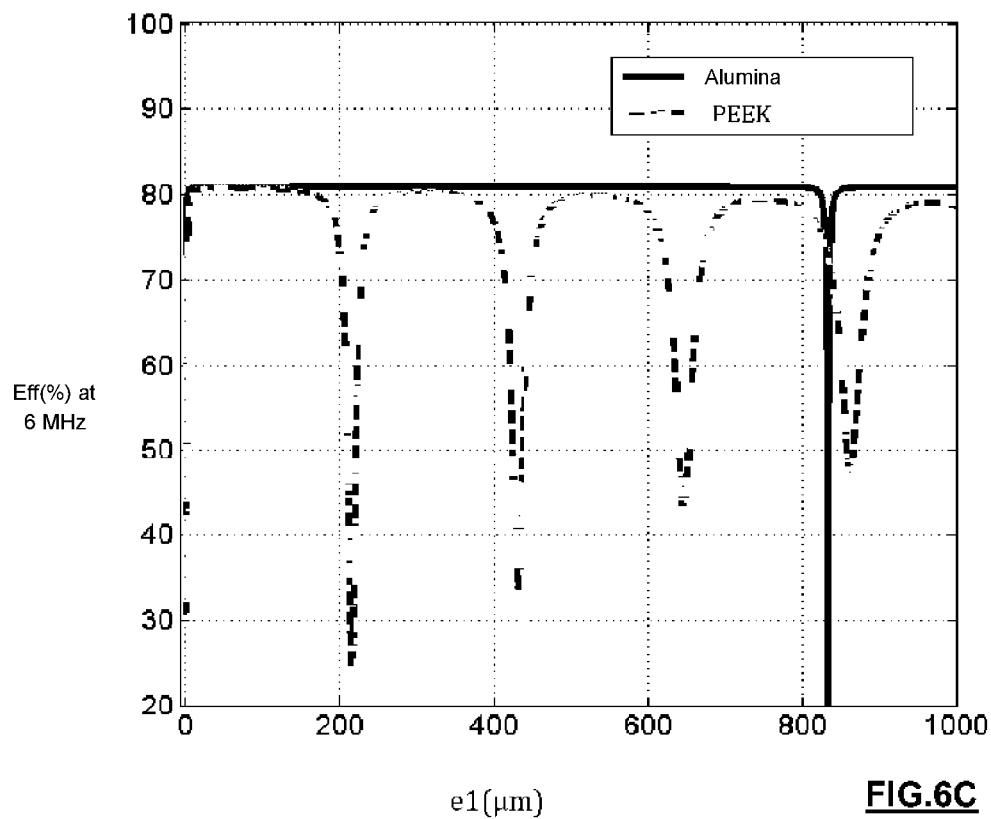

FIG. 6C illustrates the calculated reflectivity as a function of e2, also for configurations 1 and 2, e1 being fixed at the optimum (based on the value in the table). The thickness e1 of the alumina reflector is lambda/4=417 µm (black curve), and the thickness e1 of the PEEK reflector (dashed grey curve) is lambda/4=108 µm 3. Optional Features The optional features of the invention will now be described. It is clearly understood that the invention is not limited to a probe including these optional features.

Figure 4:
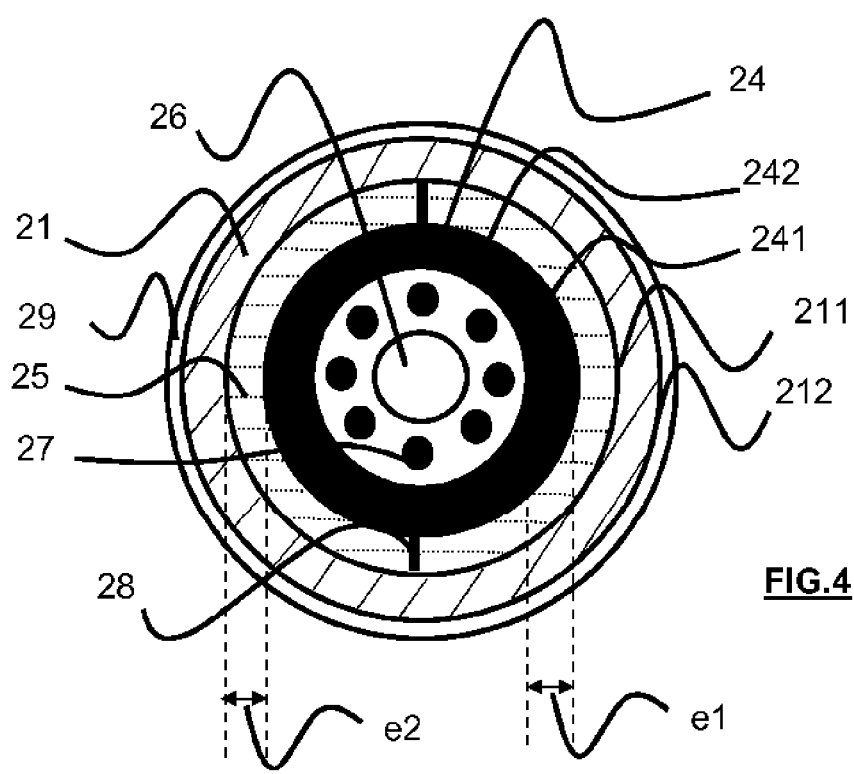

With reference to FIG. 4, an embodiment of the active portion 2 is illustrated. The transducer 21 and the reflector 24 are of the same type as in the example illustrated in FIG. 3 and will not be described in greater detail.

In this embodiment, the central channel 26 constitutes a biopsy channel for the possible collection of a portion of an organ or of a tissue so as to perform examinations. The reader will appreciate that the biopsy channel can be constituted by the tube 24 itself, without adding an additional central channel 26.

The circulation of the cooling fluid is ensured by the duct defined by the rear face 211 of the transducer 21 and the first face 241 of the internal wall 24. More precisely, the duct comprises two separation partitions 28 extending radially and allow the duct to be subdivided into two distinct chambers:
- one of the chambers allows the supply of cooling fluid, and
- the other chamber allows the discharge of the cooling fluid.

Advantageously, these two chambers communicate at their distal ends and are connected to pumps and reservoirs to allow the circulation of the cooling fluid.

The active portion 2 can also comprise one (or more) acoustic impedance adaptation layer(s) 29 covering the front face 212 of the transducer 21. The adaptation layer 29 is made of a material—such as parylene—the acoustic impedance of which is comprised between the impedance of the piezoelectric transducer 21 and the acoustic impedance of the target zone. The presence of an adaptation layer 29 allows limiting the reflection of ultrasonic waves at the interface between the transducer 21 and the external medium so as to transfer a maximum of acoustic energy to the target zone. It also allows the electrical insulation of the transducer 21. The thickness of the adaptation layer 29 is preferably equal to an integer multiple of one-quarter of the wavelength (in the material constituting the adaptation layer) at the nominal frequency of the transducer 21. The features of such an adaptation layer 29 are known to a person skilled in the art and will not be described in greater detail hereafter.

Advantageously, the central channel 26 and the internal wall 24 are coaxial. This makes it possible to balance the active portion 2. However, in other embodiments, the central channel 26 and the internal wall 24 may not be coaxial, the central channel 26 extending in the interior of the internal wall 24.

The internal wall 24 and the central channel 26 defining a free space in the interior of which electrically conducting wires 27 can be positioned to electrically connect the transducer 21 to the control unit 5. This allows the transducer 21 to be supplied with electrical energy. As a variant, the transducer 21 can be supplied with electrical power externally for example by using a flexible printed circuit connector wound around the front face 212 of the transducer 21.

Besides electrical wires 27, the free space between the central channel 26 and the internal wall 24 can contain a material with an acoustic impedance very different from that of the cooling fluid—such as air or an expanded foam. This makes it possible to guarantee that at least 90% of the incident energy propagating toward the internal wall 24 is reflected toward the transducer 21.

Figure 5:
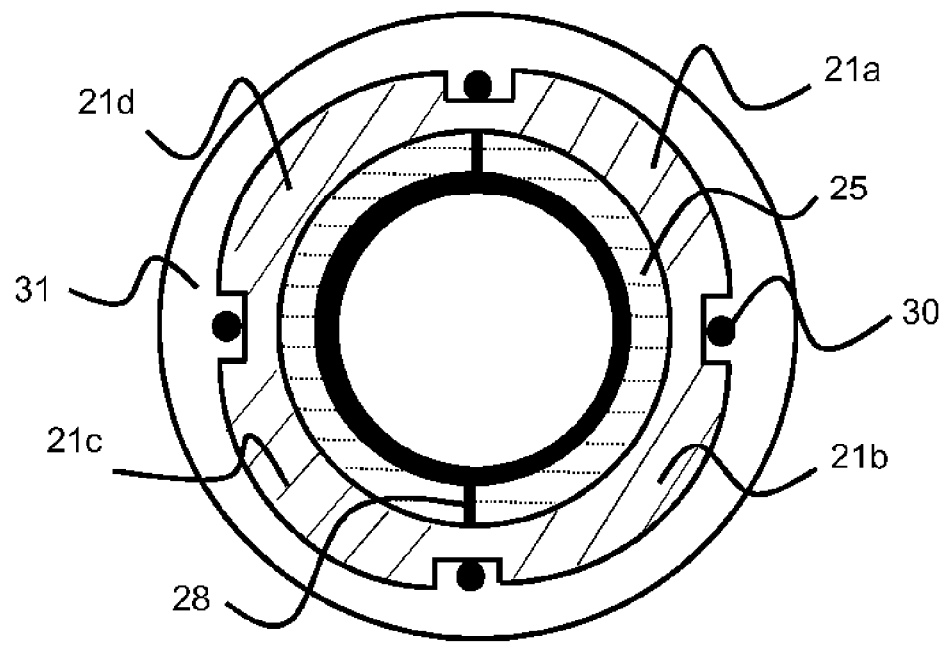

With reference to FIG. 5, another embodiment of the active portion is illustrated.

This embodiment differs from the embodiment illustrated in FIG. 4 in that the transducer 21 is composed of four piezoelectric element assemblies 21a-21d obtained by segmentation of a one-piece tubular transducer by means of a high-power laser or mechanical milling allowing the formation of longitudinal grooves. These longitudinal grooves can then be used for the passage of cables 30 for connecting the different piezoelectric elements 21a-21d. Each assembly can comprise six to eight (or more) piezoelectric elements lengthwise. Advantageously, the different piezoelectric elements (numbering 24 or 32) can be controlled independently. This allows the treatment to be adjusted depending on the size of the tumor—and in particular on its longitudinal extension.

The longitudinal grooves (in reality, the non-emitting portions of the transducers) must be rather thin so as not to reduce the acoustic radiation diagram of the elements. If this were the case, a "petal" diagram would be obtained instead of a circular one. By way of indication, the width of the grooves must be less than the wavelength in the front propagation medium, and the sum of the width of the grooves must be less than one-eighth of the perimeter of the exterior of the probe. For example, the width of the grooves must be less than 300 microns for a transducer of 4 elements with an external diameter of 3.5 mm operating at 4 MHz.

The active portion also comprises a cuff 31 with a variable volume extending on the exterior face of the transducer 21.

The cuff 31 is connected to fluid supply means (gas or liquid) allowing its volume to be varied between:
  a retracted conformation where the volume of the cuff is a minimum, and
  a deployed conformation (as illustrated in FIG. 5) where the volume of the cuff is a maximum.

For example, the cuff can be connected to the cooling system 7 for supplying cooling fluid 25 to the active portion 2. In this case, the cuff constitutes a duct for carrying the cooling fluid; the cooling system 7 feeds the interior of the active portion 2 with cooling fluid and this is returned to the cooling system 7 through the cuff 31.

The presence of a cuff 31 has numerous advantages. In particular, the cuff 31 allows the tissue in proximity to the probe to be cooled as well as the front face of the transducer. The cuff also forms a means of electrical insulation of the probe.

4. Method of Manufacture

Figure 7:
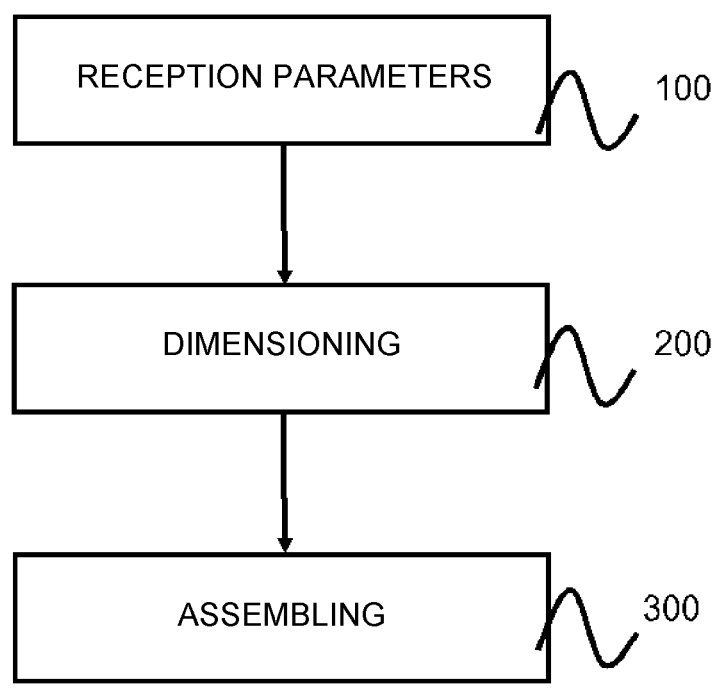
FIG. 7 is a schematic view of different steps of a method of designing a treatment probe.

With reference to FIG. 7, an example of a method of design of an ultrasonic probe for heating a target medium is illustrated.

The method comprises a step 100 consisting of reception of the desired operating parameters for the probe. These parameters depend in particular on the application intended for the treatment probe. These parameters comprise, non-exhaustively:
  The nominal frequency of use of the transducer,
  The presence or absence of a biopsy channel,
  The type of material desired for the reflector,
  The type of material situated on the second face of the reflector,
  The type of cooling fluid used, etc.

The method then comprises a step 200 consisting of dimensioning the probe. This step consists in particular of defining an optimal thickness of the layer of cooling fluid so that a secondary ultrasonic wave emanating from the rear face of the transducer and propagating toward the front face interferes constructively with a primary ultrasonic wave emanating from the front face of the transducers, the thickness of said layer of cooling fluid being calculated based on:
  the material constituting the cooling fluid,
  the thickness and the material constituting the internal wall,
  the central resonance frequency.

Finally, the method comprises a step 300 consisting of assembling the different elements constituting the probe.

5. Conclusions

The combination of a reflector and of a cooling fluid on the rear face of the transducer allows an intra-tissue treatment probe to be obtained:
  the effectiveness of which is close to that of an ultrasonic thermal ablation probe in which the rear face of the transducer is covered with a layer of air,
  while limiting the local increase in temperature of the transducer.

The reader will have understood that numerous modifications can be applied to the invention described previously without departing materially from the new teachings and advantages described here.

In particular, the optimized thickness e2 of the layer of fluid and that e1 of the internal tube can be fairly close (+/−25%)—without being rigorously equal—to a multiple (even or odd) of one-quarter or of one-half of the wavelength.

Likewise, even if, in the different embodiments presented previously, the thickness of the cooling fluid was fixed, it could be variable, for example by using a flexible and compressible material for constituting the internal wall. In this case, a variation of the pressure of the cooling fluid could allow the thickness of the layer of cooling fluid to be varied. For example, and increase (respectively a reduction) of the pressure of the cooling fluid allows and increase (respectively a decrease) in the thickness of the layer of cooling fluid. This variation of the pressure of the cooling fluid can advantageously be controlled by means provided in the generator 6 and the control unit 5. In particular, the generator 6 can include one (or more) coupler(s) which make it possible to measure the voltage, the current or the power transmitted or reflected by the probe. When the thickness of the fluid layer varies, the secondary wave is reflected more or less toward the transducer, with manifests itself by variations in the measurements carried out by the coupler. These measurements are interpreted in the control unit 5 and inform the user on the condition of the probe, for example on the pressure of its cooling liquid. Consequently, all modifications of this type are designed to be incorporated within the scope of the attached claims.

The invention claimed is:

1. An ultrasonic probe for heating, internally, an ultrasonically absorbent target medium, the probe comprising:
  at least one piezoelectric transducer including a front face designed to be positioned facing the target medium and a rear face opposite to the front face, the transducer being capable of emitting at least one primary wave emanating from its front face and at least one secondary wave emanating from its rear face,
  a reflector facing the rear face of the transducer, the reflector being designed to reflect the secondary wave emitted by the transducer,
  a layer of cooling fluid between the transducer and the reflector,
  wherein the thickness of the layer of cooling fluid is designed based on:
    the material constituting the cooling fluid,
    the thickness and the material constituting the reflector,
    the nominal frequency of the transducer,
  so that a secondary ultrasonic wave reflected by the reflector and propagating toward the front face interferes constructively with a primary ultrasonic wave emanating from the front face of the transducer.

2. The ultrasonic probe according to claim 1, wherein the transducer is supplied with electrical power by an electrical excitation signal inducing the emission by said transducer of ultrasonic waves at a nominal frequency comprised between 3 and 10 MHz, the reflector being designed to reflect at least 80% of the acoustic energy of the secondary wave emitted by the transducer at the nominal frequency of the transducer, and the cooling fluid having an acoustic attenuation coefficient of less than 1 dB/cm at the nominal frequency of the transducer, preferably less than 0.1 dB/cm at the nominal frequency of the transducer.

3. The probe according to claim 1, wherein, depending on the thickness and on the material constituting the reflector, the thickness of the layer of cooling fluid is:
either equal to an odd multiple of one-quarter of the wavelength of the secondary ultrasonic wave in the constitutive material of the cooling fluid,
or equal to an integer multiple of one-half of the wavelength of the secondary ultrasonic wave in the constitutive material of the cooling fluid.

4. The probe according to claim 1, wherein:
the acoustic impedance of the material constituting the reflector is greater than $10^7$ kg/(m$^2$s), and
the thickness of the layer of cooling fluid is equal to an odd multiple of one-quarter of the wavelength of the secondary ultrasonic wave in the constitutive material of the cooling fluid.

5. The probe according to claim 4, wherein the thickness of the reflector is greater than or equal to 20 μm, preferably greater than 30 μm, and even more preferably greater than 40 μm.

6. The probe according to claim 1, wherein the reflector comprises an internal wall including a first face facing the rear face of the transducer, and a second, opposite face, the second face being in contact with air.

7. The probe according to claim 6, wherein:
the acoustic impedance of the material constituting the internal wall is comprised between $1\times10^6$ kg/(m$^2$s) and $10\times10^6$ kg/(m$^2$s),
the thickness of the internal wall is equal to an odd multiple of one-quarter of the wavelength of the secondary ultrasonic wave in the material constituting the internal wall, and
the thickness of the layer of cooling fluid is equal to an odd multiple of one-quarter of the wavelength of the secondary ultrasonic wave in the cooling fluid.

8. The probe according to claim 6, wherein:
the acoustic impedance of the material constituting the internal wall is comprised between $1\times10^6$ kg/(m$^2$s) and $10\times10^6$ kg/(m$^2$s), and
the thickness of the internal wall and the thickness of the layer of cooling fluid are not comprised in ranges of more or less 25% around an integer multiple of one-half of the wavelength of the secondary ultrasonic wave in the material constituting the internal wall.

9. The probe according to claim 6, wherein:
the acoustic impedance of the material constituting the internal wall is comprised between $1\times10^6$ kg/(m$^2$s) and $10\times10^6$ kg/(m$^2$s),
the thickness of the internal wall is equal to an integer multiple of one-half of the wavelength of the secondary ultrasonic wave in the material constituting the internal wall,
the thickness of the layer of cooling fluid is equal to an integer multiple of one-half of the wavelength of the secondary ultrasonic wave in the cooling fluid.

10. The probe according to claim 6, wherein:
the acoustic impedance of the material constituting the internal wall is comprised between $1\times10^6$ kg/(m$^2$s) and $10\times10^6$ kg/(m$^2$s), and
the thickness of the internal wall and the thickness of the layer of cooling fluid are not comprised in ranges of more or less 25% around an odd multiple of one-quarter of the wavelength of the secondary ultrasonic wave in the material constituting the internal wall.

11. The probe according to claim 6, wherein the internal wall is made of a flexible and compressible material.

12. The probe according to claim 11, which further comprises a junction box mounted to a remote unit, said remote unit being configured to vary the pressure of cooling fluid within the internal wall in order to vary the thickness of the layer of cooling fluid.

13. The probe according to claim 1, which comprises an adaptation layer on the front face of the transducer, said adaptation layer having a thickness equal to a multiple of one-quarter of the wavelength of the ultrasonic wave in the constitutive material of said adaptation layer.

14. The probe according to claim 1, wherein the transducer is composed of piezoelectric elements obtained by segmentation of a one-piece tubular transducer by means of a high-power laser or mechanical milling allowing for the formation of longitudinal grooves, the width of the grooves being less than the wavelength of the primary wave, and the sum of the width of the grooves being less than one-eighth of the perimeter of the exterior of the probe.

15. The probe according to claim 1, which further comprises a cuff with a variable volume extending on the exterior face of the transducer, said cuff being connected to fluid supply means allowing a volume of the cuff to be varied between a retracted conformation where the volume of the cuff is a minimum, and a deployed conformation where the volume of the cuff is a maximum.

* * * * *